United States Patent
Hauger et al.

(10) Patent No.: US 7,901,080 B2
(45) Date of Patent: Mar. 8, 2011

(54) OPHTHALMOLOGIC SURGICAL MICROSCOPE SYSTEM HAVING AN OCT-MEASURING DEVICE

(75) Inventors: Christoph Hauger, Aalen (DE); Markus Seesselberg, Aalen (DE); Dieter Quendt, Essingen (DE)

(73) Assignee: Carl Zeiss Surgical GmbH, Oberkochen (DE)

( * ) Notice: Subject to any disclaimer, the term of this patent is extended or adjusted under 35 U.S.C. 154(b) by 64 days.

(21) Appl. No.: 12/453,349

(22) Filed: May 7, 2009

(65) Prior Publication Data

US 2009/0279052 A1 Nov. 12, 2009

(30) Foreign Application Priority Data

May 7, 2008 (DE) .................. 10 2008 022 674
Aug. 15, 2008 (DE) .................. 10 2008 041 284

(51) Int. Cl.
*A61B 3/00* (2006.01)
*G02B 21/00* (2006.01)
(52) U.S. Cl. .................. 351/246; 359/381; 359/383
(58) Field of Classification Search .................. 351/246, 351/205, 209, 210; 359/381, 382, 383, 384, 359/379, 368; 356/345
See application file for complete search history.

(56) References Cited

U.S. PATENT DOCUMENTS

| | | | |
|---|---|---|---|
| 5,321,501 A | 6/1994 | Swanson et al. | |
| 6,004,314 A | 12/1999 | Wei et al. | |
| 6,741,948 B2 | 5/2004 | Hauger et al. | |
| 6,937,390 B2 * | 8/2005 | Akiyama et al. | 359/381 |
| 7,554,723 B2 * | 6/2009 | Moeller et al. | 359/383 |
| 2002/0085208 A1 | 7/2002 | Hauger et al. | |
| 2008/0084540 A1 | 4/2008 | Gaida | |
| 2008/0117432 A1 | 5/2008 | Reimer et al. | |
| 2008/0198329 A1 | 8/2008 | Gaida | |

FOREIGN PATENT DOCUMENTS

| | | |
|---|---|---|
| DE | 102 60 256 | 7/2004 |
| WO | WO 2006/100544 | 9/2006 |

* cited by examiner

*Primary Examiner* — Hung X Dang
(74) *Attorney, Agent, or Firm* — Walter Ottesen (57) ABSTRACT

The invention is directed to an ophthalmologic surgical microscope system (100) for examining the eye of a patient. The ophthalmologic surgical microscope system includes a surgical microscope (101) as well as a carrier arrangement (102) wherein the surgical microscope (101) is accommodated so as to permit elevation adjustment in order to be able to adjust a work distance between the surgical microscope (101) and the eye of the patient. An ophthalmoscopic ancillary module (103) is connected to the surgical microscope and has an adjustable ophthalmoscopic magnifier system in order to adjust a distance between the ophthalmoscopic magnifier and the surgical microscope (101). The ophthalmologic surgical microscope system (100) has a sensor system for measuring the distance of the surgical microscope (101) from the patient eye. The sensor system is configured as an OCT-measuring device.

15 Claims, 7 Drawing Sheets

OPHTHALMOLOGIC SURGICAL MICROSCOPE SYSTEM HAVING AN OCT-MEASURING DEVICE

CROSS REFERENCE TO RELATED APPLICATIONS

This application claims priority of German patent application nos. 10 2008 022 674.2 and 10 2008 041 284.8, filed May 7, 2008 and Aug. 15, 2008, respectively, the entire contents of both applications being incorporated herein by reference.

FIELD OF THE INVENTION

The invention relates to an ophthalmologic surgical microscope system for examining a patient eye having a surgical microscope. The system further includes a carrier arrangement wherein the surgical microscope is accommodated so as to be adjustable in elevation in order to be able to adjust a work distance between the surgical microscope and the eye of the patient. The system also includes an ophthalmoscopic ancillary module having an adjustable ophthalmoscopic magnifier system in order to adjust a distance between the ophthalmoscopic magnifier and the surgical microscope as well as a sensor system for measuring the distance of the surgical microscope from the patient eye.

BACKGROUND OF THE INVENTION

An ophthalmologic surgical microscope system of the kind described above is disclosed in United States patent publication 2008/0084540 A1. This ophthalmologic surgical microscope system includes a surgical microscope which is accommodated in a carrier arrangement so as to be adjustable in elevation in order to be able to adjust a work distance between the surgical microscope and a patient eye. A first drive is provided for positioning the surgical microscope in elevation. The ophthalmologic surgical microscope system has an ophthalmoscopic ancillary module having an ophthalmoscopic magnifier system arranged thereon so as to be displaceable. For this system, a further drive is provided which permits a work distance to be set between an ophthalmoscopic magnifier and the patient eye. In that a sensor is integrated in the surgical microscope system for measuring the distance from the surgical microscope and the patient eye, the system setting which is always advantageous can be displayed to the operator by means of a position display and it is possible to displace the ophthalmologic surgical microscope system via a control unit in such a manner that movements of the patient eye are automatically compensated.

SUMMARY OF THE INVENTION

It is an object of the invention to provide an ophthalmologic surgical microscope which permits a position determination of the surgical microscope above a patient eye with good accuracy.

This object is achieved with an ophthalmologic surgical microscope system of the kind described above wherein the sensor system is configured as an OCT-measuring device (OCT=Optical Coherence Tomography).

An OCT-measuring device permits the non-invasive display and measurement of structures within a tissue by means of optical coherence tomography. As an optical image providing method, the optical coherence tomography permits generating especially section images or volume images of biological tissue with micrometer resolution. A corresponding OCT-system includes a source for time-dependent incoherent and spatial coherent light having a coherence length $L_c$ which is supplied to a specimen beam path and a reference beam path. The specimen beam path is directed to the tissue to be examined. Laser radiation, which is radiated back into the specimen beam path because of scatter centers in the tissue, superposes the OCT-system with laser radiation from the reference beam path. An interference signal arises because of the superposition. The position of scatter centers for the laser radiation in the examined tissue can be determined from this interference signal.

For OCT-systems, the configuration principle of the time-domain OCT and of the Fourier-domain OCT are known.

The configuration of a time-domain OCT is described, for example, in U.S. Pat. No. 5,321,501 with reference to FIG. 1a and column 5, line 40, to column 11, line 10. In such a system, the optical path length of the reference beam path is continuously varied via a rapidly moving reference mirror. The light from the specimen beam path and the reference beam path is superposed on a photo detector. When the optical path lengths of the specimen beam path and the reference beam path are coincident, an interference signal arises on the photo detector.

A Fourier-domain OCT is, for example, explained in published United States patent publication 2009/0015842. In order to measure the optical path length of a specimen beam path, light from the specimen beam path is, in turn, superposed on light from a reference beam path. As a difference to a time-domain OCT, for a measurement of the optical path length of the specimen beam path, the light from the specimen beam path and the reference beam path are not directly conducted to a detector; instead, the light is first spectrally dispersed by means of a spectrometer. The spectrum intensity of the superposed signal so generated from the specimen beam path and the reference beam path is then detected with a detector. By evaluating the detector signal, the optical path length of the specimen beam path is, in turn, determined.

The OCT-measuring device of the ophthalmologic surgical microscope system of the invention contains a component assembly for generating an OCT-scanning beam path from short coherent laser radiation with an analyzer unit for evaluating interference signals.

Such an OCT-measuring device can perform a very precise distance measurement while utilizing IR-radiation which is non-damaging for a patient eye because especially the boundary surfaces of structures can be detected by means of an OCT-measuring device which structures are transparent for visible light.

According to a further embodiment of the invention, the specimen beam path of the OCT-measuring device is conducted onto the viewing field of the surgical microscope. In this way, a position determination of the surgical region relative to the surgical microscope is possible.

In a further embodiment of the invention, the specimen beam path of the OCT-measuring beam path passes through the ophthalmoscopic magnifier when viewing with the ophthalmoscopic magnifier. In this way, it is possible to determine the distance of the ocular fundus of the eye of the patient from the surgical microscope.

In a further embodiment of the invention, the ophthalmoscopic magnifier has a layer reflecting OCT-measuring radiation. In this way, the position of the ophthalmoscopic magnifier relative to the patient eye is reliably detected.

In a further embodiment of the invention, the layer of the ophthalmoscopic magnifier, which reflects the OCT-measuring radiation, is configured on the side of the ophthalmoscopic magnifier facing toward the patient eye. In this way, a reliable measurement of the distance between the ophthalmoscopic magnifier and the patient eye is possible by means of OCT-measuring radiation.

In a further embodiment of the invention, the OCT-measuring device is configured as an OCT-system having an XY-scanning unit. In this way, a two-dimensional topography of the patient eye and especially the curvature and apex point position of the cornea can be measured with the system. This permits to display to a viewing person the precise position of the pupil of the patient eye with reference to the ophthalmologic surgical microscope system. In this way, a viewing person is placed in the position to position the ophthalmoscopic magnifier ahead of the cornea of the patient eye in such a way that the exit pupil of the ophthalmologic surgical microscope system and the pupil of the patient eye mutually overlap. This makes possible especially the viewing of the ocular fundus of the eye with the ophthalmologic surgical microscope system without shading.

In a further embodiment of the invention, the OCT-measuring device is configured as a dual-beam interferometer, especially, as a dual-beam interferometer as disclosed in FIG. 2 of published United States patent application 2002/0085208 or with reference to FIG. 2 or FIG. 5 in German published patent application 102 60 256 A1.

In a further embodiment of the invention, the reference branch of the OCT-measuring device corresponds to any favorable work distance of the surgical microscope from the patient eye. In this way, an adaptation of the OCT-measuring device to the corresponding ophthalmologic surgical microscope is effected.

In a further embodiment of the invention, an XY-positioning unit is provided in the ophthalmologic surgical microscope system. In this way, a precise centering of the surgical microscope above a patient eye is made possible. A central position of the surgical microscope can be detected by means of the OCT-measuring device.

In a further embodiment of the invention, the XY-positioning device for positioning the ophthalmologic surgical microscope relative to the patient eye is coupled to the OCT-measuring device in the ophthalmologic surgical microscope system. In this way, an automatic centering of the ophthalmologic surgical microscope system above the patient eye is possible.

In a further embodiment of the invention, an open-loop control mode or a closed-loop control mode can be activated in the ophthalmologic surgical microscope system in order to configure the ophthalmologic surgical microscope system during continuous position detection by means of the OCT-measuring device above the patient eye for an optimal work adjustment.

In a further embodiment of the invention, the ophthalmologic surgical microscope system includes a handheld keypad by means of which tissue structures of the patient eye can be marked which are displayed on a monitor in order to trigger an automatic focusing onto these tissue structures.

An ophthalmologic surgical microscope system according to the invention permits the surgical microscope thereof to be positioned above the patient eye with the following method steps: inputting a favorable position of at least one of the surgical microscope and the ophthalmoscopic magnifier relative to the patient eye; determining the position of at least one of the surgical microscope and the ophthalmoscopic magnifier relative to the patient eye utilizing the OCT-measuring device; determining a deviation of the measured position of at least one of the surgical microscope from the patient eye and the ophthalmoscopic magnifier to the favorable position; and, shifting the position of at least one of the surgical microscope and the ophthalmoscopic magnifier by the determined deviation.

The surgical microscope of the invention can also be positioned above the patient eye with the following method steps: inputting a favorable position of at least one of the surgical microscope and the ophthalmoscopic magnifier relative to the patient eye; determining the distance of at least one of the surgical microscope and the ophthalmoscopic magnifier from the patient eye utilizing the OCT-measuring device; determining a deviation of the measured distance of at least one of the surgical microscope and the ophthalmoscopic magnifier from the patient eye at the favorable position; and, adjusting at least one of the work distance of the surgical microscope and of the ophthalmoscopic magnifier to the favorable position.

In addition, the surgical microscope of the invention can be positioned above the patient eye with the following method steps: inputting a favorable position of at least one of the surgical microscope and the ophthalmoscopic magnifier relative to the patient eye; shifting the position of at least one of the surgical microscope and the ophthalmoscopic magnifier by a determined deviation; and, utilizing the OCT-measuring device for continuously checking the position of at least one of the surgical microscope and the ophthalmoscopic magnifier from the patient eye.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
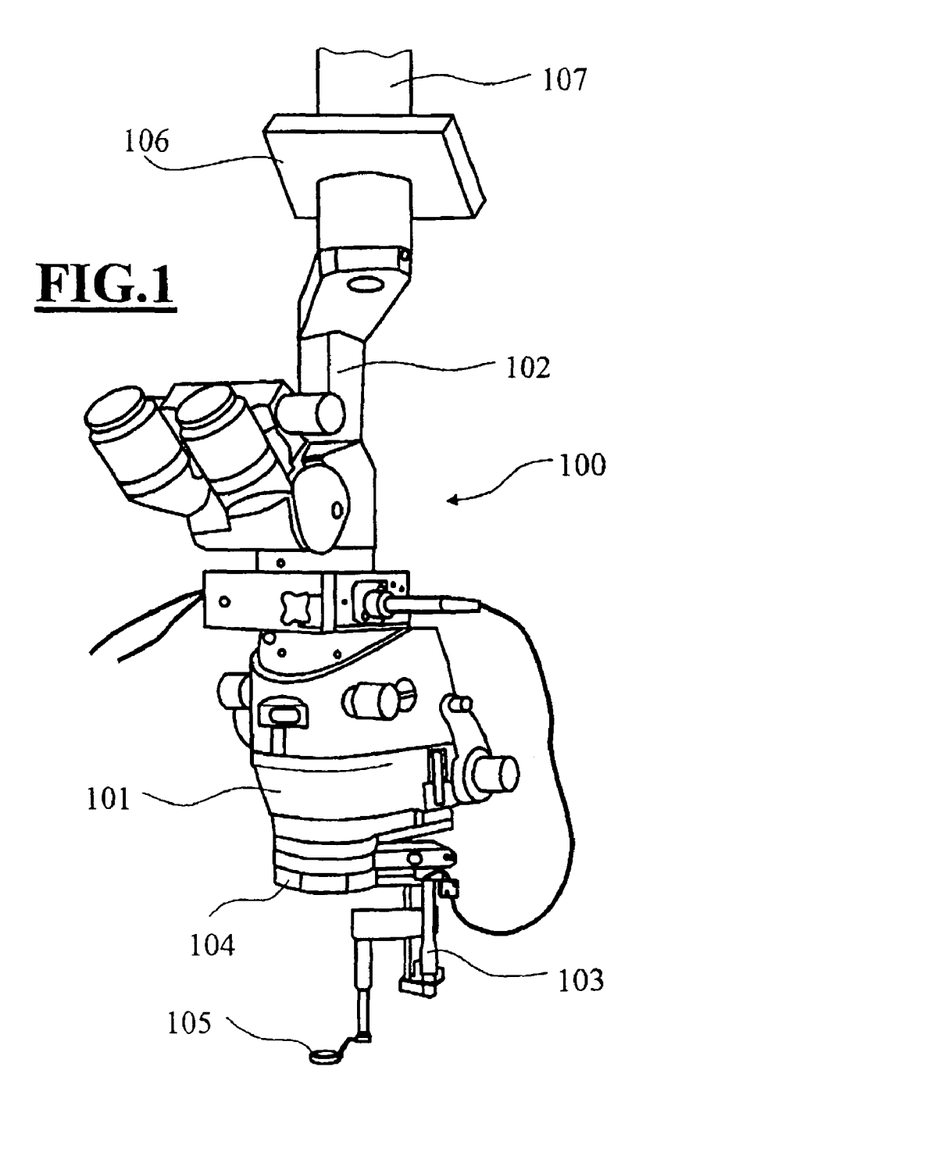
FIG. 1 is a perspective schematic of an ophthalmologic surgical microscope system having a surgical microscope with an OCT-measuring device and with the surgical microscope accommodated in an XY-positioning device.

The surgical microscope system 100 shown in FIG. 1 includes a surgical microscope 101 which is accommodated in a carrier unit adjustable in elevation. An ophthalmoscopic ancillary unit 103 having a reduction lens 104 and an ophthalmoscopic magnifier 105 is connected to the surgical microscope 101. The surgical microscope 101 is held on the carrier arrangement 102 via an XY-positioning device 106. The carrier arrangement 102 is, in turn, accommodated on a carrier arm 107 of a surgical microscope stand (not shown).

The configuration of the surgical microscope system 100 of FIG. 1 will now be explained with respect to FIG. 2.

Figure 2:
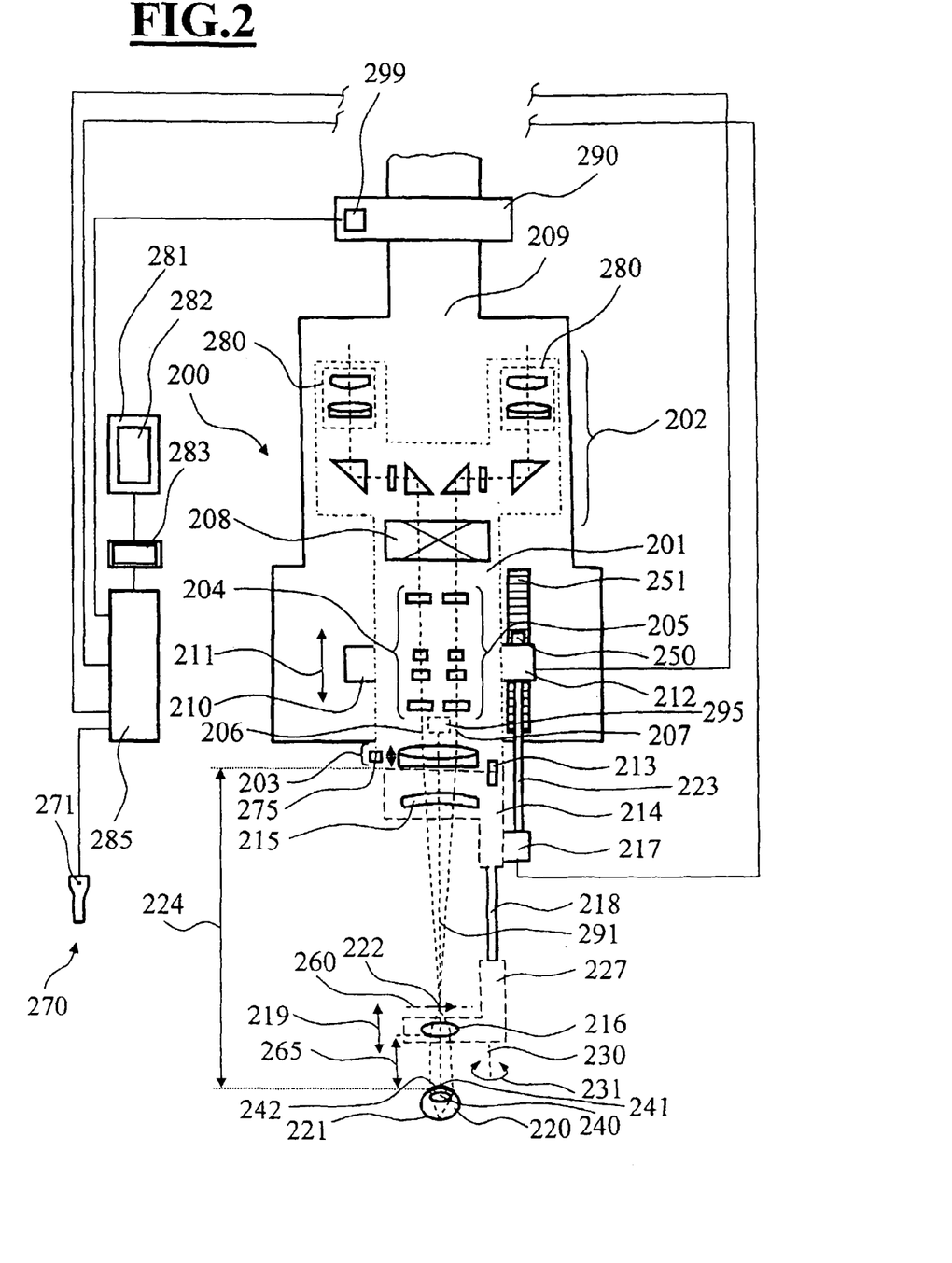
FIG. 2 is a schematic showing the configuration of the ophthalmologic surgical microscope system of FIG. 1.

The ophthalmologic surgical microscope system 200 of FIG. 2 includes a surgical microscope 201 which is configured as a stereo microscope. The surgical microscope 201 has two viewing tubes 202 having respective oculars 280 and a main objective system 203 having a variable focal length. A controllable drive 275 is assigned to the main objective system 203. The main objective system 203 having variable focal length permits the work distance 224 to be adjusted in the surgical microscope 201 in the range of 200 mm to 500 mm. The surgical microscope 201 further includes a pancratic magnification system (204, 205) for the left and right binocular viewing beam paths (206, 207). A switchable system for beam transposition and image inversion 208 is arranged between the pancratic magnification system 204 and the viewing tube unit 202.

The surgical microscope is accommodated on a carrier unit 209 with an XY-positioning device 290. With a focusing unit 210, the surgical microscope can be moved up and down in correspondence to the double arrow 211. In this way, the work distance 224 can be adjusted between the surgical microscope main objective system 203 and an eye 220 of a patient being examined. The surgical microscope is so focused onto the object region which is to be examined.

A motoric drive 212 is assigned to the focusing device 210. The motoric drive 212 is connected to a toothed wheel gear 250 which meshes with a toothed rack 251 on the carrier arrangement 209.

The ophthalmologic surgical microscope system 200 further includes an ophthalmoscopic ancillary module 214. The ophthalmoscopic ancillary module 214 is connected via a pivot joint 213 to the surgical microscope 201.

The ophthalmoscopic ancillary module 214 includes a reduction lens 215 as well as an ophthalmoscopic magnifier 216. The ophthalmoscopic magnifier 216 is accommodated in an ophthalmoscopic magnifier holder 227. The ophthalmoscopic magnifier holder 227 can be moved up and down by means of a drive 217 above the eye 220 of a patient to be examined in correspondence to double arrow 219. The drive 217 acts on a worm gear 218. The drive 212 for adjusting the surgical microscope 201 and the drive 217, which moves the ophthalmoscopic magnifier 216, are operatively connected via a coupling 223. This coupling 223 is configured as a mechanical coupling in the ophthalmologic surgical microscope system 200.

Because of the refractive power of the lens 240 in a patient eye 220, it is necessary for the examination of the ocular fundus 221 of a patient eye 220 with a surgical microscope 201 to image the ocular fundus 221 in an intermediate image plane 260 on which the viewing beam paths (206, 207) of the surgical microscope are focused. This is the function of the ophthalmoscopic magnifier 215. The ophthalmoscopic magnifier 216 generates in the intermediate image plane 260 a laterally inverted intermediate image 222 of the ocular fundus 221 of the patient eye 220. In order to be able to sharply view this intermediate image 222, the focus plane of the viewing beam paths (206, 207) of the surgical microscope 201 must be coincident with the intermediate image plane 260.

When the ophthalmoscopic ancillary module 214 is pivoted into the viewing beam paths (206, 207) of the ophthalmologic surgical microscope system 200, a switchable system for beam transposition and image inversion 208 in the surgical microscope 201 ensures that an erect image of the ocular fundus 221 of the eye 220 of the patient can be viewed in the viewing tube unit 202 of the surgical microscope 201.

The reduction lens 215 in the ophthalmoscopic ancillary module 214 increases the refractive power of the main objective system 203 of the surgical microscope 201. The reduction lens 215 effects a shifting of the focus plane of the viewing beam paths (206, 207) of the surgical microscope 201 toward the main objective system 203 of the surgical microscope 201.

The pivot joint 213 permits the ophthalmoscopic ancillary module 214 to pivot about the axis 230 in correspondence to the double arrow 231 into and out of the viewing beam paths (206, 207) of the surgical microscope. The refractive power and arrangement of the reduction lens 215 in the ophthalmoscopic ancillary module 214 are so selected that, for a pivoting of the ophthalmoscopic ancillary module 214 out of the viewing beam paths (206, 207), the focusing plane of the viewing beam paths is shifted by approximately 2.5 cm in the direction of the patient eye 220 under examination. For an outpivoted ophthalmoscopic ancillary module 214, this permits the lens 240 of the patient eye 220 to be sharply viewed with the ophthalmologic surgical microscope system 200 without it being necessary to refocus the surgical microscope 201.

For positioning the surgical microscope relative to the patient eye, the surgical microscope system 200 includes an OCT-measuring device 295 which makes available the OCT-scanning beam 291. The OCT-scanning beam 291 passes through the microscope main objective system 203 and also the reduction lens 215 and the ophthalmoscopic magnifier 216 when the ophthalmoscopic ancillary module 214 is pivoted into the viewing beam path (206, 207) of the ophthalmologic surgical microscope system.

The OCT-scanning beam 291 is a short coherent light in the wavelength range 700 μm to 1500 μm. The OCT-measuring device permits to measure the topography of the patient eye 220 and, especially, to determine the work distance 224 of the surgical microscope 201 from the patient eye 220 as well as the distance 265 of the ophthalmoscopic magnifier 216 from the patient eye 220.

The ophthalmologic surgical microscope system 200 includes a display device 281 which is connected to an operator-controlled unit 283 and the OCT-measuring device 295. The display device 281 has a monitor 282 which can be activated via an operator-controlled unit 283. Accordingly, a viewing person has the possibility of: a display of the work distance 224 of the surgical microscope 201 to the patient eye 220; the display of the distance of the ophthalmoscopic magnifier 216 to the patient eye 220 with this distance being detected via the OCT-measuring device 295; and, the display of the position of the apex 241 of the cornea 242 of the patient eye 220 with reference to the optical axis of the main objective system 203. Furthermore, via the display device, tissue structures and section images of the patient eye 220 can be visualized which were stored in a memory (not shown).

This permits a viewing person to configure the ophthalmologic surgical microscope system 200 with good operating comfort for an optimal distance 265 from patient eye 220 and an ophthalmoscopic magnifier 216. On the one hand, it can be ensured that the patient eye 220 is not touched by the ophthalmoscopic magnifier 216 and, on the other hand, it is ensured that no shading of the viewed image from the ocular fundus of the patient eye 220 takes place as a consequence of too great a distance of the ophthalmoscopic magnifier 216 from the patient eye 220.

The ophthalmologic surgical microscope system 200 can be operated in an open-loop control mode or, alternatively, in a closed-loop control mode for an automated adjustment of an optimal work position. For this purpose, the ophthalmologic surgical microscope system 200 includes an open-loop and closed-loop control unit 285 which is connected to the following: the OCT-measuring device 295; a drive 299 of the XY-positioning device 290; the focusing unit 210; the motoric drive 212; and, the drive 217 which operates on the ophthalmoscopic magnifier 216 via the worm gear 218.

As an alternative to the manual adjustment of the ophthalmologic surgical microscope system 200, it is also possible to configure the system in an open-loop control mode or a closed-loop control mode, that is, like an autofocus system with continually running position detection via the OCT-measuring device 295 above the patient eye 220 for an optimal work position.

The configuration of the OCT-measuring device 295 of FIG. 2 will now be explained with reference to FIG. 3.

The OCT-measuring device 295 includes a unit 301 for generating and analyzing an OCT-scanning beam path. The unit 301 is integrated into the surgical microscope 101 of FIG. 1. The unit 301 can, however, also be arranged outside of the surgical microscope, for example, in a corresponding stand console. The unit 301 is connected to a light conductor 303 which makes available an OCT-scanning beam 304. The OCT-scanning beam 304 exits from the light conductor 303 at the exit end 320 thereof and is conducted via a first scan mirror 305 and via a second scan mirror 306 of the OCT-scan unit 307. After the OCT-scan unit 307, the scanning beam passes through a converging lens 308 and passes through the main objective system 309.

The light conductor exit end 320 can be moved by a drive 321 in correspondence to the double arrow 322 parallel to the optical axis 323 of the main objective system 309 of the surgical microscope.

For the examination of the ocular fundus 392 of the patient eye 390, the opthalmoscopic ancillary module 103 is switched into the optical viewing beam path in the ophthalmologic surgical microscope system 100 of FIG. 1.

In this case, the OCT-scanning beam 304 passes through the reduction lens 315 and through the ophthalmoscopic magnifier 316. The refractive power and position of the converging lens 308 is so selected that an imaging of the exit end 320 of light conductor 303 takes place on the cornea 391 of the patient eye 390 via the main objective system 309 and the reduction lens 315 as well as the ophthalmoscopic magnifier 316. On the end facing toward the patient eye 390, the ophthalmoscopic magnifier 316 has a layer 318 which is transparent for visible light and which at least partially reflects the OCT-scanning beam 304.

Figure 4:
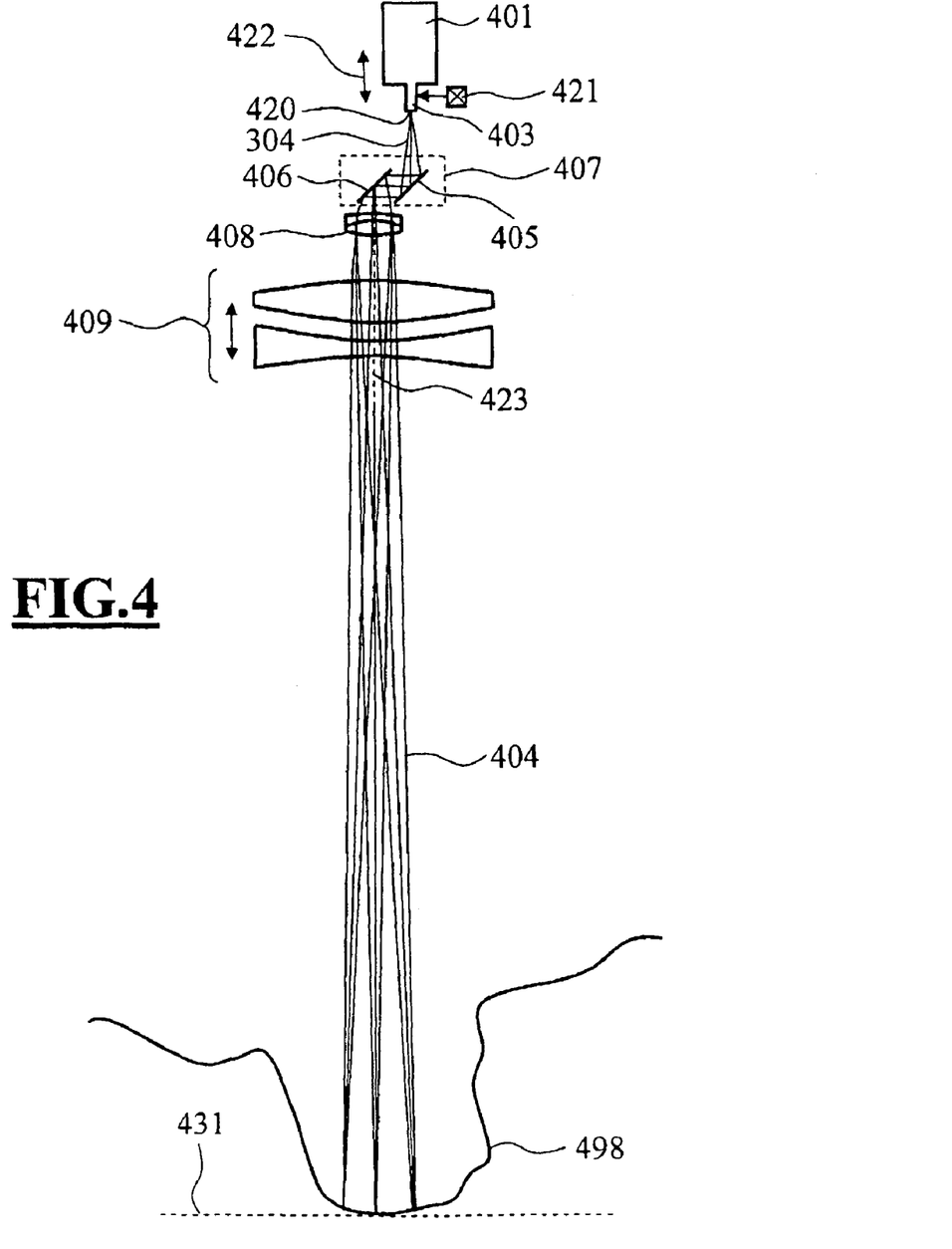
FIG. 4 is a schematic showing the course of the OCT-scanning beam path on the surgical microscope of the system of FIG. 1 when the ophthalmoscopic ancillary module 103 is pivoted out of the viewing beam path.

FIG. 4 shows the course of the OCT-scanning beam on the surgical microscope 101 of FIG. 1 when the ophthalmoscopic ancillary module 103 is pivoted out of the viewing beam path.

Figure 3:
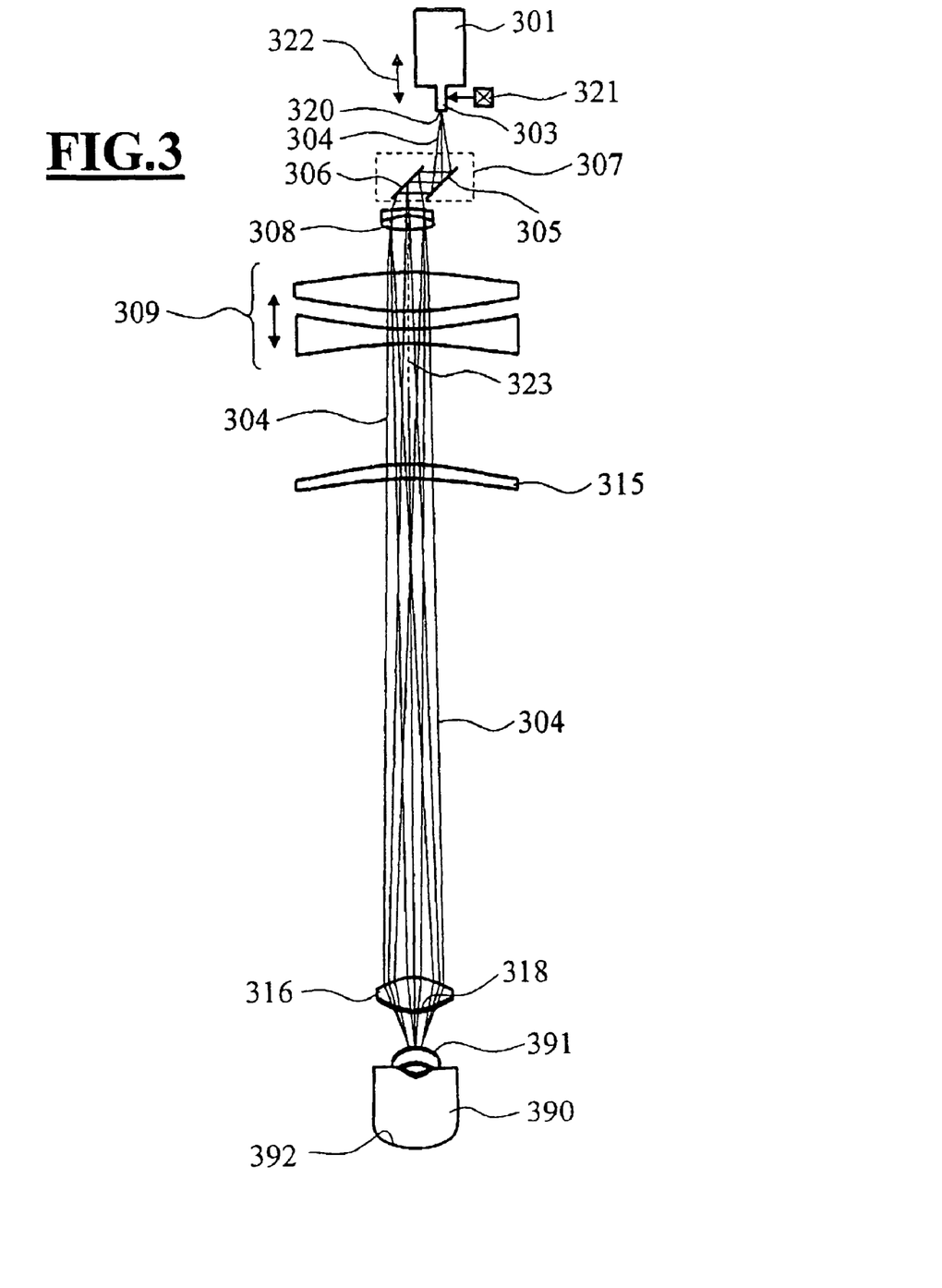
FIG. 3 is a schematic showing the configuration of the OCT-measuring device of the ophthalmologic surgical microscope system of FIGS. 1 and 2.

Insofar as the component assemblies shown in FIG. 4 correspond to those of FIG. 3, the reference numerals used in FIG. 4 are increased by the number 100 in comparison to FIG. 3.

For the case of the ophthalmoscopic ancillary module being pivoted out of the viewing beam path, the light conductor exit end 420 of the light conductor 403 is positioned via the drive 421 in such a manner that the OCT-scanning beam 404 is conducted via the scan mirrors 405 and 406, the converging lens 408 as well as the main objective system 409 directly to the object region 498. The light conductor exit end 420 is then conjugated to the object plane 431 of the ophthalmologic surgical microscope.

Figure 5:
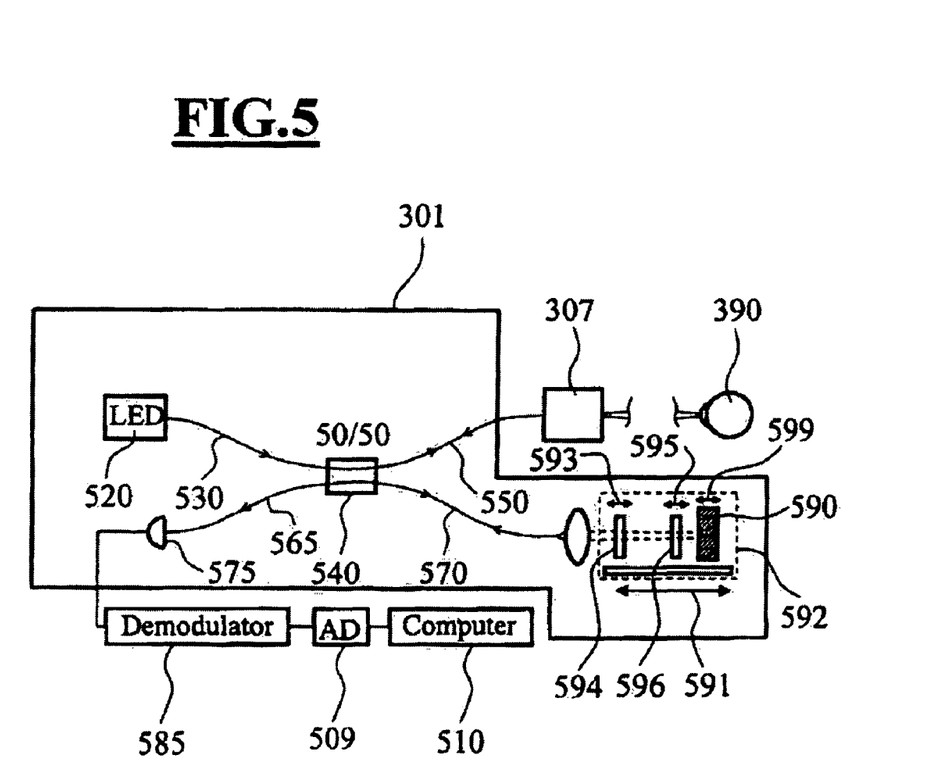
FIG. 5 is a schematic showing the unit for generating and analyzing the OCT-scanning beam path of the OCT-measuring device.

FIG. 5 shows the configuration of the unit 301 for generating and analyzing the OCT-scanning beam of FIG. 3. The unit is configured as a dual-beam time-domain OCT. The unit could, however, also be configured as a Fourier-domain OCT.

In the unit, a superluminescence diode 520 is provided whose light is coupled into an optical fiber 530. This light is split by a 50%/50% optical coupler 540 into a specimen branch with optical. fiber 550 and a reference branch with optical fibers 565 and 570. The light from the specimen branch reaches the patient eye 390 via the OCT-scan unit.

A reference mirror 590 is mounted in the reference branch. This reference mirror 590 is mounted on a displacer unit 592 and is movable for rapid linear movement in correspondence to the double arrow 599. The displacer unit 592 is movable in correspondence to the double arrow 591. In addition, on the displacer unit 592, a first partially reflective mirror 594 is mounted movable in correspondence to the double arrow 593 and a second partially reflective mirror 596 is also disposed on the displacer unit and is movable in correspondence to the double arrow 595.

The light, which is reflected by the reference mirror 590 and the partially reflecting mirrors (594, 596), generates together with the light from the specimen branch an interference signal when optical wavelengths in the specimen and reference branches correspond to each other.

This interference signal is detected by a photodetector 575 and is conducted to an evaluation by a computer 510 via a demodulator 585 and an A/D converter 509.

The displacer unit 592 is provided for an adjustment range which permits the reference mirror 590 to be shifted for an optical wavelength range which corresponds to the variation range for the work distance which can be adjusted with the surgical microscope 201 in FIG. 2.

The linearly movable reference mirror 590 can be moved with an axial stroke on the displacer unit 592 in correspondence to the double arrow 599. This stroke is 2 mm. It is, however, advantageous to provide for a stroke in the range of 2 mm to 10 mm for the linearly movable reference mirror. With this stroke, the entire eyeball of a patient eye can be scanned and measured via OCT scanning.

Figure 6:
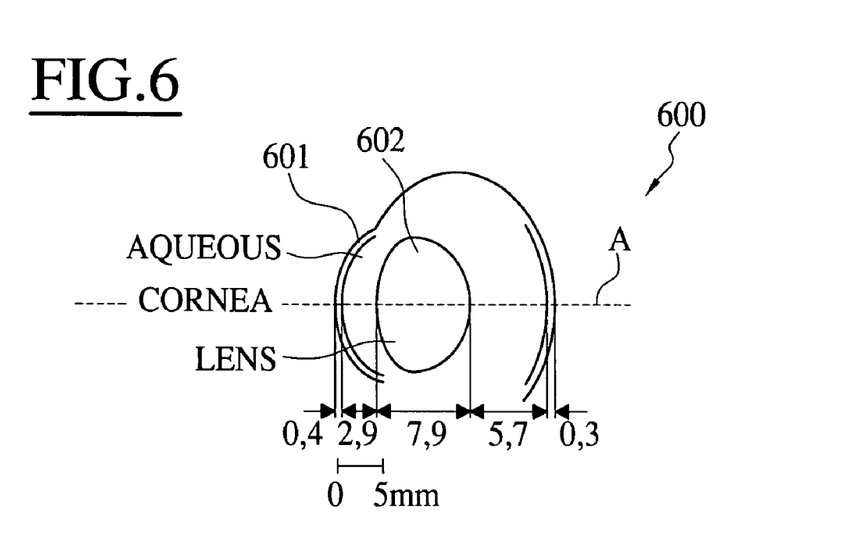
FIG. 6 is a schematic representation of an eye of a patient.
Figure 7:
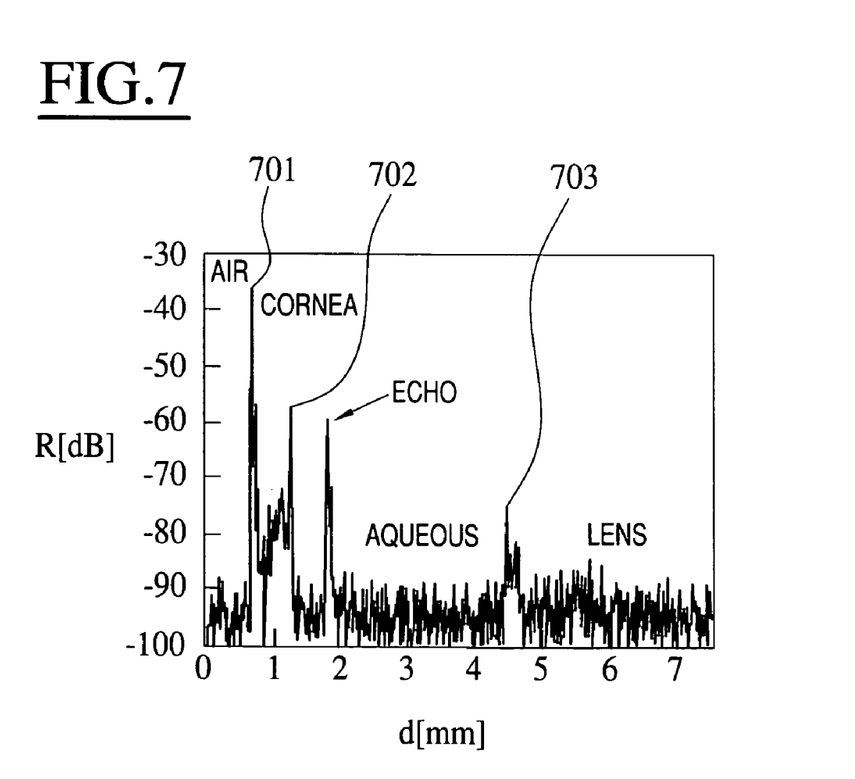
FIG. 7 shows the reflection characteristic of a typical patient eye for OCT-scanning radiation; and, FIG. 8 is a schematic of an ophthalmologic surgical microscope system which incorporates an illuminating unit and control unit connected to the OCT-measuring device.

FIGS. 6 and 7 show how the OCT-scanning signal is produced with this signal being detectable at a patient eye. FIG. 6 shows the schematic configuration of a patient eye 600. In FIG. 7, the relative reflectivity R in dB referred to 100% reflection capacity for different ranges of the patient eye 600 is plotted along the axis A. With the OCT-measuring device 295 in the surgical microscope 201 of FIG. 2, the spatial distance of the light conducting exit end to the scatter centers in the object region can be measured. The more scattering centers that are available in the examined tissue via OCT-scanning radiation, the more pronounced and stronger is the OCT-scanning signal. An OCT-scanning signal for patient eye 600 in FIG. 6 has, for the cornea and the eye lens 602, characteristic measurement signal peaks 701, 702 and 703 which correspond to tissue structures of the patient eye 600, namely, the boundary surfaces of the cornea and of the eye lens facing toward the cornea.

The OCT-measuring device 295 in FIG. 2 is adjusted in such a manner to the main objective system 203 with variable focal length that OCT-measurement signals from the focus plane of the main objective system 203 can always be detected. This is achieved in that the length of the reference branch of the OCT-measuring device 295 is readjusted and caused to track in correspondence to the displacement of the focus plane 431 in FIG. 4. In this way, the main objective system 203 can be automatically adjusted for a work distance in dependence upon the detected OCT-signal.

The position of the partially reflecting mirrors 594 and 596 in the displacer unit is preferably so selected that it corresponds to an optical wavelength in the reference branch which has a correspondence in the optical wavelength for an optimal arrangement of the ophthalmoscopic magnifier 216 of FIG. 2 in the specimen beam path.

Furthermore, an OCT-measuring device permits image-providing transparent structures of the patient eye to be measured utilizing so-called B-scans and C-scans and to store the positions of detected tissue structures in a data memory to be then able to automatically focus the ophthalmologic surgical microscope in a targeted manner onto these structures. This OCT-measuring device could be like the OCT-measuring device 295 in the ophthalmologic surgical microscope system 200 of FIG. 2. For this kind of operation of the ophthalmologic surgical microscope system, a control via a handheld keypad 270 shown in FIG. 2 is advantageous. This handheld keypad includes a function key 271 with which tissue structures, which are displayed on the monitor 282 of the display device 281, can be marked and then trigger a focusing on these structures.

It is noted that the OCT-measuring device 295 need not necessarily be configured as a dual-beam interferometer; rather, a simple reference branch for OCT radiation can also be provided such as in the OCT-measuring device which is described with respect to FIG. 2 in U.S. Pat. No. 6,004,314. It is also possible to configure the OCT-measuring device 295 as a non-scanning OCT-measuring device, that is, a system wherein no scanning mirrors are provided.

When an OCT-measuring device having a scanning unit is provided, the curvature and the apex point position of the cornea of a patient eye can be measured and this data can be applied for adjusting the XY-positioning device of the system. Such an OCT-measuring device can also measure the curvature and the apex point position of the ophthalmoscopic magnifier utilized in the system. When using different ophthalmoscopic magnifiers, this permits also a precise distance determination of the particular ophthalmoscopic magnifier to the patient eye. Furthermore, this permits determination of an optimal position of the ophthalmoscopic magnifier relative to the patient eye in three dimensions, that is, not only the optimal distance of the ophthalmoscopic magnifier to the patient eye but also its most favorable position in XY-direction, that is, the plane perpendicular to the optical axis of the main objective system 203 in the surgical microscope 200 of FIG. 2.

Furthermore, it is possible to configure the OCT-measuring device, in which a reference branch for short coherent light is provided, as a system with variable reference branch length as well as with a fixed reference branch length. It is advantageous here to provide a reference branch length which is designed as a configuration of the system for the optimal distances in the ophthalmologic microscope system. The optimal adjustment of the system can preferably be made known to a viewing person via a sound signal.

In lieu of an external monitor in the ophthalmologic surgical microscope 200 shown in FIG. 2, alternatively, or in addition, corresponding position data with reference to the surgical microscope system relative to the examined patient eye can be made visible in the optical viewing beam path of the surgical microscope by reflecting data in. It is advantageous to display to the viewing person an optimal apparatus setting via an acoustic or optical signal.

Figure 8:
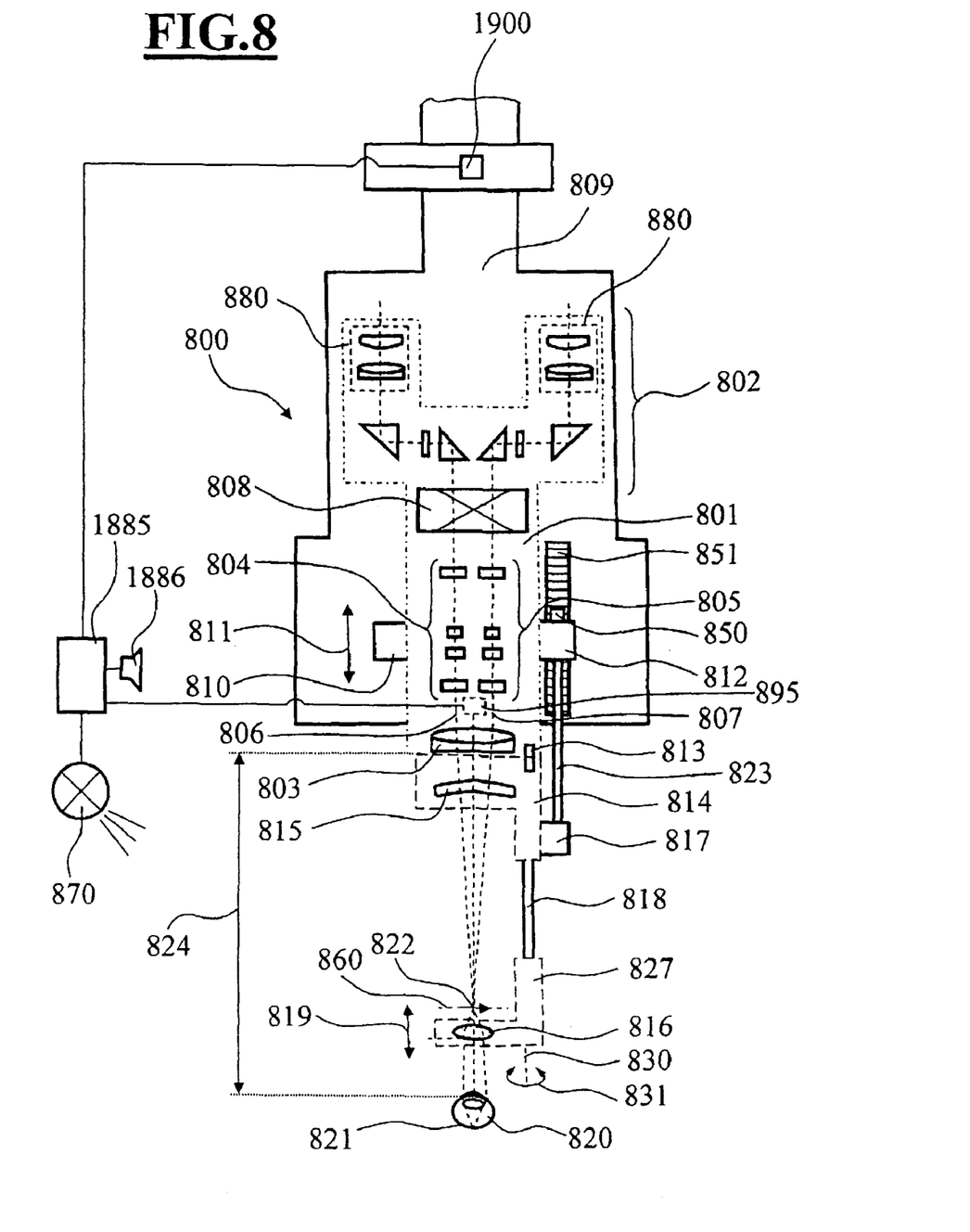

FIG. 8 shows an ophthalmologic surgical microscope system 800 having a controllable illumination unit 870. Insofar as the component assemblies of the ophthalmologic surgical microscope system 800 correspond to those in the ophthalmologic surgical microscope system 200 of FIG. 2, these component assemblies are provided with a reference numeral increased by 600 in comparison to FIG. 2.

With the OCT-measuring device 295, it is possible to detect whether biological tissue is disposed in the object region examined with the surgical microscope and which type of tissue is disposed there. With this information, the radiation intensity of the illuminating system in the surgical microscope can be correspondingly varied or it is possible to display a warning signal to a viewing person in order to minimize the danger of burning biological tissue with the illuminating system of the surgical microscope.

The OCT-measuring device 895 is connected to a control unit 1885 for this purpose.

The control unit 1885 predetermines a defined illuminating intensity to the illuminating system 870 in dependence upon a distance signal detected via the OCT-measuring device 895 and generates an acoustical or optical warning signal by means of a signal generator 1886 when the measuring signal of the OCT-measuring device 895 corresponds to specific biological types of tissue which are especially sensitive to the illuminating light.

Furthermore, a control unit 1895 is provided in the ophthalmologic surgical system which receives a distance signal from the OCT-measuring device 895 and which functions to control stand brakes 1900. If a deviation of the work distance 824 of the patient eye 820 to a favorable work distance is detected by the OCT-measuring device 895, then the control unit 1895 triggers a closing of the stand brakes 1900 and an acoustic warning signal or, alternatively, also an optical warning signal is displayed to the viewing person.

It is understood that the foregoing description is that of the preferred embodiments of the invention and that various changes and modifications may be made thereto without departing from the spirit and scope of the invention as defined in the appended claims.

What is claimed is:

1. An ophthalmologic surgical microscope system for examining a patient eye, the system comprising:
   a surgical microscope;
   a carrier arrangement for accommodating said surgical microscope so as to be positionable in elevation in order to adjust a work distance between said surgical microscope and the patient eye;
   an ophthalmoscopic ancillary module including: an ophthalmoscopic magnifier and a drive to adjust a distance between said ophthalmoscopic magnifier and said surgical microscope;
   a sensor system for measuring said work distance of said surgical microscope from the patient eye; and,
   said sensor system being configured as an OCT-measuring device.

2. The ophthalmologic surgical microscope system of claim 1, wherein said surgical microscope defines a viewing field and said OCT-measuring device includes a specimen beam path conducted to said viewing field.

3. The ophthalmologic surgical microscope system of claim 2, wherein said specimen beam path of said OCT-measuring device passes through said ophthalmoscopic magnifier when a viewing person views therewith.

4. The ophthalmologic surgical microscope system of claim 3, wherein said ophthalmoscopic magnifier has a layer reflecting OCT-measuring radiation.

5. The ophthalmologic surgical microscope system of claim 4, wherein said ophthalmoscopic magnifier has a side facing toward the patient eye and said layer is formed on said side.

6. The ophthalmologic surgical microscope system of claim 1, wherein said OCT-measuring device is configured as an OCT-system having an XY-scan unit.

7. The ophthalmologic surgical microscope system of claim 1, wherein said OCT-measuring device is configured as a dual-beam interferometer.

8. The ophthalmologic surgical microscope system of claim 1, said OCT-measuring device including a reference branch and said reference branch corresponding to a favorable work distance of said surgical microscope from the patient eye.

9. The ophthalmologic surgical microscope system of claim 1, further comprising an XY-positioning unit for positioning the surgical microscope relative to the patient eye.

10. The ophthalmologic surgical microscope system of claim 9, wherein said XY-positioning unit is coupled to said OCT-measuring device.

11. The ophthalmologic surgical microscope system of claim 1, further comprising means for activating a control mode for configuring said ophthalmologic surgical microscope system for an optimal work setting while said OCT-measuring device continuously detects position above the patient eye.

12. The ophthalmologic surgical microscope system of claim 1, further comprising a monitor and a handheld keypad with which tissue structures displayed on said monitor can be marked in order to trigger an automatic focusing on said tissue structures.

13. A method for positioning a surgical microscope of an ophthalmologic surgical microscope system above a patient eye, the ophthalmologic surgical microscope system further including a carrier arrangement for accommodating said surgical microscope so as to be positionable in elevation in order to adjust a work distance between said surgical microscope and the patient eye; an ophthalmoscopic ancillary module including: an ophthalmoscopic magnifier and a drive to adjust a distance between said ophthalmoscopic magnifier and said surgical microscope; and, an OCT-measuring device for measuring said work distance of said surgical microscope from the patient eye; the method comprising the steps of:
  inputting a favorable position of at least one of said surgical microscope and said ophthalmoscopic magnifier relative to the patient eye;
  determining the position of at least one of said surgical microscope and said ophthalmoscopic magnifier relative to the patient eye utilizing said OCT-measuring device;
  determining a deviation of the measured position of at least one of said surgical microscope from the patient eye and said ophthalmoscopic magnifier to said favorable position; and,
  shifting the position of at least one of said surgical microscope and said ophthalmoscopic magnifier by the determined deviation.

14. A method for positioning a surgical microscope of an ophthalmologic surgical microscope system above a patient eye, the ophthalmologic surgical microscope system further including a carrier arrangement for accommodating said surgical microscope so as to be positionable in elevation in order to adjust a work distance between said surgical microscope and the patient eye; an ophthalmoscopic ancillary module including: an ophthalmoscopic magnifier and a drive to adjust a distance between said ophthalmoscopic magnifier and said surgical microscope; and, an OCT-measuring device for measuring said work distance of said surgical microscope from the patient eye; the method comprising the steps of:
  inputting a favorable position of at least one of said surgical microscope and said ophthalmoscopic magnifier relative to the patient eye;
  determining the distance of at least one of said surgical microscope and said ophthalmoscopic magnifier from the patient eye utilizing said OCT-measuring device;
  determining a deviation of the measured distance of at least one of said surgical microscope and said ophthalmoscopic magnifier from the patient eye at said favorable position; and,
  adjusting at least one of said work distance of said surgical microscope and of said ophthalmoscopic magnifier to said favorable position.

15. A method for positioning a surgical microscope of an ophthalmologic surgical microscope system above a patient eye, the ophthalmologic surgical microscope system further including a carrier arrangement for accommodating said surgical microscope so as to be positionable in elevation in order to adjust a work distance between said surgical microscope and the patient eye; an ophthalmoscopic ancillary module including: an ophthalmoscopic magnifier and a drive to adjust a distance between said ophthalmoscopic magnifier and said surgical microscope; and, an OCT-measuring device for measuring said work distance of said surgical microscope from the patient eye; the method comprising the steps of:
  inputting a favorable position of at least one of said surgical microscope and said ophthalmoscopic magnifier relative to the patient eye;
  shifting the position of at least one of said surgical microscope and said ophthalmoscopic magnifier by a determined deviation; and,
  utilizing said OCT-measuring device for continuously checking the position of at least one of said surgical microscope and said ophthalmoscopic magnifier from the patient eye.

\* \* \* \* \*